United States Patent [19]

Mitra et al.

[11] Patent Number: 4,689,323
[45] Date of Patent: Aug. 25, 1987

[54] COVALENTLY BOUND HEPARIN—ANTITHROMBIN-III COMPLEX

[75] Inventors: Gautam Mitra, Kensington; Robert E. Jordan, Walnut Creek, both of Calif.

[73] Assignee: Miles Laboratories, Inc., Elkhart, Ind.

[21] Appl. No.: 536,072

[22] Filed: Sep. 26, 1983

[51] Int. Cl.[4] .................... A61K 31/725; C08B 37/10
[52] U.S. Cl. ........................................ 514/56; 536/21; 514/822
[58] Field of Search .................. 424/183; 536/21; 514/56, 822

[56] References Cited

U.S. PATENT DOCUMENTS 4,301,153 11/1981 Rosenberg .
4,446,126 5/1984 Jordan .............................. 424/183

FOREIGN PATENT DOCUMENTS 0048898 4/1982 European Pat. Off. ............ 424/183

OTHER PUBLICATIONS

Bjork et al., Permanent Activation of Antithrombin by Covalent Attachment of Heparin Oligosaccharides, FEBS Letters, 143(1), pp. 96–100 (1982).
Ceustermans et al., Preparation, Characterization, and Turnover Properties of Heparin—Antithrombin III Complexes Stabilized by Covalent Bonds, J. Biol. Chem. 257(7), pp. 3401–3408 (1982).
Hoylaerts et al., Covalent Complexes Between Low Molecular Weight Heparin Fragments and Antithrombin III–Inhibition Kinetics and Turnover Parameters, Chem. Abs. 98:213439k (1983).
Miura et al., Anticoagulant Activity of Artificial Biomedical Materials with Co-Immobilized Antithrombin III and Heparin, Biochimie 62, pp. 595–601 (1980).
Jordan et al., Fractionation of Low Molecular Weight Heparin Species and Their Interaction with Antithrombin, J. Biol. Chem. 254(8), pp. 2902–2913 (1979).
Tam et al, Proc. Natl. Acad. Sci., 73 (6), 2128 (1976).
Marshall et al, J. Biol. Chem., 254(4), 1081 (1976).
Kohn et al, Enzyme Microb. Technology, 4, 161 (1982), and Biochem. Biophys. Res. Commun., 107 (3), 878 (1982).
Rao et al, Thromb. Res., 24, 181 (1981).
Bonen et al, Thromb. Res., 27, 123 (1982).
Baird et al, J. Bone Jt. Surg., 59A, 1061 (1977).
Rosenberg et al, Proc. Natl. Acad. Sci., 75 (7), 3065 (1978).
Rosenberg et al, Biochem. Biophys. Res. Commun., 86 (4), 1319 (1979).
Lam et al, Biochem. Biophys. Res. Commun., 69 (2), 570 (1976).
Hook et al, FEBS Letters 66 (1), 90 (1976).

*Primary Examiner*—Johnnie R. Brown
*Assistant Examiner*—John W. Rollins, Jr.
*Attorney, Agent, or Firm*—Pamela A. Simonton

[57] ABSTRACT

There is disclosed a process for producing a covalently bound heparin—antithrombin-III complex useful for anticoagulant therapy, a covalently bound heparin—antithrombin-III complex produced by the process, a composition thereof in a pharmaceutically acceptable carrier, and a method for preventing and treating thromboembolisms by administering to a human patient a therapeutically effective amount of the complex or preparation.

36 Claims, No Drawings

COVALENTLY BOUND HEPARIN—ANTITHROMBIN-III COMPLEX

BACKGROUND OF THE INVENTION

1. Field of the Invention

This invention relates to a new anticoagulant for human use and to a process for producing and a method for using the new anticoagulant.

Heparin ("Hep") is a known blood anticoagulant that functions by binding tthe inhibitor, antithrombin (antithrombin-III or "AT-III"), and by accelerating the rate at which this inhibitor neutralizes serum proteases of the coagulation system. Heparin has been fractionated into components having varying degrees of activity and there is evidence which suggests that only a very small proportion of unfractionated heparin constitutes that component which is characterized by relatively high specific activity.

Although unfractionated heparin alone is routinely employed for the treatment of thromboembolism or for the prevention of clot formation in at-risk patients, problems concerning side effects and efficacy have been pointed out. By the expression "at-risk patients" is meant those patients prone to develop thromboembolisms. For example, Rao et al, *Thromb. Res.*, 24, 181 (1981) and Boneu et al, *Thromb. Res.*, 27, 123 (1982) have noted that continuous intravenous infusion of heparin results in a decrease (about 35%) in plasma antithrombin-III ("AT-III") levels in all thromboembolic patients receiving heparin therapy. These patients may be at an enhanced risk. Baird et al, *J. Bone Jt. Surg.*, 59A, 1061 (1977), report recurrent arterial thrombosis in patients on systemic heparin therapy.

Further, although the administration of antithrombin has been proposed as a means at controlling undesirable clot-formation in at-risk patients, especially for those patients having congenital antithrombin deficiency, this therapy would require very large amounts of antithrombin and frequent administration of antithrombin since it has a plasma half-life of about three days.

Antithrombin - heparin complexes have been reported and proposed for therapeutic use in anticoagulant therapy. Further, preparation of such a complex in pharmaceutically useful amounts has been reported.

2. Related Application

U.S. Ser. No. 357,504, filed Mar. 12, 1982, a continuation-in-part of U.S. Ser. No. 192,170, filed Sept. 30, 1980 and now abandoned, both being owned by the assignee of the present application, discloses an antithrombin-high activity heparin complex produced by contacting a lectin-containing, water-insoluble matrix with antithrombin and heparin to allow (1) the antithrombin tbind reversibly with the matrix and (2) the high activity heparin component of heparin to complex with the antithrombin, washing the matrix tremove unbound heparin, contacting the matrix with a solution of a carbohydrate having the ability tdisplace the antithrombin-high activity heparin complex, and recovering the complex free of uncomplexed heparin and antithrombin.

3. Description of the Prior Art

Rosenberg et al, *Proc. Natl. Acad. Sci.*, 75 (7), 3065 (1978), disclose the fractionation of porcine heparin species of low molecular weight into highly active and relatively inactive fractions by a 2-cycle affinity technique based on the affinity of heparin for antithrombin. There were obtained three heparin fractions, namely (1) a "highly active heparin" from Cycle I of the process, and (2) an "active" and (3) a "relatively inactive" heparin species both from Cycle II of the process. "Active" and "highly active" heparin species were each obtained as a complex with antithrombin after separation from unbound heparin by gel filtration on Sephadex G-100. The "highly active heparin"-antithrombin complex was obtained in Cycle I by chromatography of a mixture of antithrombin and low molecular weight heparin at a molar ratiof 0.08/1.0. The "active heparin"-antithrombin complex was obtained in Cycle II by similarly chromatographing a mixture of antithrombin and the residual unbound heparin from Cycle I at a molar ration of 1.5/1.0. Both of these heparin fractions were separated from antithrombin in separate, subsequent chromatography steps on G-100 in the presence of 3 M NaCl. "Relatively inactive" heparin was obtained in Cycle II as that fraction of heparin which did not bind to antithrombin. The resulting highly active, active and relatively inactive heparin species were subjected to analysis tdetermine their relative abundance, specific anticoagulant activity, composition and structure.

Rosenberg et al, *Biochem. Biophys. Res. Commun.*, 86 (4), 1319 (1979), disclose the results of a study of the anticoagulant activity of porcine heparin fractions obtained by gel filtration and affinity fractionation and provide the first demonstration that heparin molecules may bear multiple binding sites for antithrombin.

Rosenberg, U.S. Pat. No. 4,301,153, discloses a heparin preparation which exhibits elevated anticoagulant activity and a process for producing the preparation. Conventional, heterogenous heparin is incubated with antithrombin-III, the "heparin cofactor", and a portion of the heparin forms a complex with antithrombin-III. The uncomplexed and complexed heparin fractions are separated, and the complexed fraction is broken down to obtain antithrombin-III and an "active" form of heparin.

Jordan et al, *J. Biol. Chem.*, 254 (8), 2902 (1979), disclose the preparation of low molecular weight porcine heparin having average specific anticoagulant activity of 94 units/mg and affinity fractionation thereof, using techniques described in the Rosenberg references mentioned above, intforms having varying degrees of activity with respect tthe affinity of heparin for binding with antithrombin. Further, the reference discloses the results of the examination of the ability of the active heparin fraction, especially the highly active heparin fraction, to accelerate the thrombin - antithrombin interaction which demonstrated that heparin functions as a catalyst in the thrombin - antithrombin interaction.

Lam et al, *Biochem, Biophys. Res. Commun.*, 69 (2), 570 (1976), disclose the fractionation of heparin intactive and inactive forms by sucrose density gradient centrifugation of heparin mixed with antithrombin - thrombin cofactor and the first demonstration that only a small fraction of a given heparin preparation can bind to antithrombin - thrombin cofactor and is responsible for its distinctive anticoagulant effect.

Hook et al, *FEBS Letters*, 66 (1), 90 (1976), disclose the separation of high-activity heparin and low-activity heparin by affinity chromatography on an antithrombin substituted affinity matrix. For example, bovine antithrombin was coupled via amingroups tcyanogen bromide activated Sepharose ® 4B (Pharmacia Fine Chemicals, Uppsala, Sweden) in the presence of excess heparin (radioactive heparin previously treated with acetic anhydride in order to acetylate any free amingroups) added tshield the heparin binding sites of the antithrombin molecule from binding tthe Sepharose beads. Affinity chromatography of heparin on the immobilized antithrombin was carried out by applying samples of heparin, in 1 ml of 0.2 M NaCl-0.1 M Tris HCl, pH 7.4, to a column containing 3 ml of antithrombin—Sepharose gel equilibrated with the same buffer at 4° C. After washing with buffer until the effluent was free of uronic acid and radioactivity, the adsorbed heparin was eluted with a linear salt gradient, that is, buffered 3 M NaCl. Two distinct fractions were obtained. A portion of the material, low-affinity heparin, was obtained in the break-through fraction (or effluent) and another portion, high-affinity heparin, was obtained during gradient elution.

All of the foregoing antithrombin - heparin complexes, however, are ionic association complexes (not covalently linked) and upon infusion into small animals have not shown significant prolongation of anticoagulant properties compared to heparin controls. Dissociation of the ionic complex and subsequent inactivation of the components by ordinary biological means immediately following infusion is a likely explanation of this observation.

If dissociation of the ionic complex has been the major factor resulting in no significant prolongation of anticoagulant properties of the ionic complexes, then covalent attachment between antithrombin-III and heparin was conceived as a solution to this problem. According to this conception, heparin, a sulfonated linear mucopolysaccharide with a mean molecular weight range of 7,600–19,700 (polymeric size range of 5,000–30,000 daltons), has hydroxyl groups which could be expected to be available for activation, in liquid phase, by cyanogen halides in basic pH conditions of about 10.7–11.0. The resulting imidocarbonate could then be coupled to purified antithrombin-III at about pH 9.0 and the residual active groups neutralized with glycine. Support, by analogy, for this concept is found in Tam et al, *Proc. Natl. Acad. Sci.*, 73 (6), 2128 (1976) who demonstrated that, using dextran as the carbohydrate, a cyanogen bromide coupled dextranhemoglobin complex was cleared from circulation much more slowly than was free hemoglobin. Also, Marshall et al, *J. Biol. Chem.*, 254 (4), 1081 (1976) similarly formed a covalent dextran—trypsin conjugate using cyanogen bromide and demonstrated that intramolecular cross-linking of the protein by polysaccharide results in stabilization of the tertiary structure. Further, Kohn et al, *Enzyme Microb. Technol.* 4, 161 (1982) and *Biochem. Biophys. Res. Commun.*, 107 (3), 878 (1982), describe the results of a study of the mechanism of CNBr activation of polysaccharide resins like Sepharose and Sephadex and a new approach for the chemical reaction of Sepharose with CNBr, respectively.

Covalent complexes between heparin and antithrombin have been reported. Hoylaerts et al, *Thromb. Haemostas.*, (Stuttgart), 49 (2), 109 (1983), and Ceustermans et al, *J. Biol. Chem.*, 257 (7), 3401 (1982), disclose the chemical coupling of high affinity heparin fragments of low molecular weight heparin and of intact high affinity heparin to antithrombin-III to yield covalent complexes which inhibited factor Xa with a second order rate constant similar to those obtained for antithrombin-III saturated with heparin fragments and to that obtained for the covalent complex between antithrombin-III and native high affinity heparin. Primary amino groups, which were introduced in the high affinity fraction by N-sulfation followed by substitution with hexamethylenediamine, were reacted under basic conditions of pH with tolylene-2,4-diisothiocyanate and the isothiocyanate-containing intermediate was extracted and reacted in buffer solution at basic pH and at 30° C. with antithrombin. The resulting mixture of antithrombin-III, heparin and their covalent complex was separated by affinity chromatographic and ion exchange techniques.

Bjork et al, *FEBS Letters*, 143 (1), 96 (1982), disclose the permanent activation of antithrombin by covalent attachment to high affinity heparin oligosaccharides, which oligosaccharides were obtained by treatment of heparin with nitrous acid thus leading to formation of fragments having 2,5-D-anhydromannose residues with reactive aldehyde functions at their reducing terminals. The oligosaccharides thus obtained were covalently attached to antithrombin by a procedure based on the formation of a labile Schiff's base between the anhydromannose residue of the oligosaccharide and the amino group of a neighboring lysine residue of the protein.

DESCRIPTION OF THE INVENTION

Summary of the Invention

This invention is a process for producing a covalently bound complex of heparin (Hep) with antithrombin-III (AT-III), a complex (Hep—AT-III complex) produced by the process according to the invention, a pharmaceutical preparation comprising the Hep—AT-III complex and a pharmaceutically acceptable carrier, and a method for preventing and treating thromboembolisms comprising administering to a human patient a therapeutically effective amount of the complex or preparation according to the invention.

DETAILED DESCRIPTION OF THE INVENTION

Broadly, this invention is:

A process for producing a covalently bound heparin—anti-thrombin-III complex useful for anticoagulant therapy which comprises the steps of:

(a) contacting unfractionated or fractionated heparin containing components of varying degrees of activity, from highly active to relatively inactive, with cyanogen bromide to obtain an activated heparin intermediate; and (b) contacting the activated heparin intermediate from step (a) with antithrombin-III to obtain a mixture of a covalently bound complex of heparin and antithrombin-III (Hep—AT-III complex), free heparin and free antithrombin-III.

It is to be understood that some of the free heparin and free antithrombin-III obtained in step (b) above, and in step (b) in the preferred, more preferred, and most preferred embodiments according to the invention described below, can associate together and be present in the mixture obtained in step (b) in the form of a non-covalent, or ionic, association or complex.

Preferably, the process for producing a covalently bound heparin—antithrombin-III complex useful for anticoagulant therapy according to the invention defined above comprises the additional step of:

(c) processing the mixture of the covalently bound heparin—antithrombin-III complex, free heparin and free antithrombin-III from step (b) to separate therefrom free heparin to obtain a mixture of the covalent Hep—AT-III complex and free AT-III.

The mixture of the covalently bound heparin—antithrombin-III complex and free heparin and free antithrombin-III from step (b) can be processed to provide a pharmaceutical preparation which can be used for anticoagulant therapy in human patients. Or, preferably, the mixture from step (b) above can be processed as in step (c) above to separate free heparin from the mixture from step (b) to obtain a mixture of the covalently bound heparin—antithrombin-III complex and free antithrombin-III. It is to be understood that the processing set forth in step (c) for separating and removing free heparin would remove both free heparin and heparin non-covalently associated with free antithrombin-III in the mixture obtained step (b) above.

Suitable techniques for processing the mixture to separate the free heparin therefrom to obtain the mixture of the covalently bound Hep—AT-III complex and Free AT-III include (1) contacting the mixture with a lectin-containing proteinaceous matrix, for example, an affinity chromatography matrix such as is described in the Rosenberg, Jordan and Hook references mentioned above, (2) ion exchange chromatography techniques which are effective to separate free heparin from the Hep—AT-III complex and free AT-III, (3) eletrophoretic separation techniques, and (4) immobilized antibodies with affinity for antithrombin.

The mixture of the covalently bound Hep—AT-III complex and free AT-III can be processed to provide a pharmaceutical preparation which can be used for anticoagulant therapy, that is, to prevent and to treat thromboembolisms in human patients. Or, more preferably the mixture from step (c) above can be further processed to separate therefrom free AT-III to obtain the covalent Hep—AT-III complex. Suitable techniques for separating the free AT-III from the Hep—AT-III complex include (1) contacting the mixture of the Hep—AT-III complex and free AT-III with an affinity chromatography matrix, for example a heparin-agarose matrix as is disclosed by Bjork et al or on heparin-Ultrogel as is disclosed by Ceustermans et al mentioned above, (2) ion exchange chromatography techniques which are effective to separate free AT-III from the Hep—AT-III complex, and (3) electrophoretic separation techniques.

More preferably, the process for producing a covalently bound heparin—antithrombin-III complex useful for anticoagulant therapy according to the invention comprises the steps of:

(a) contacting unfractionated or fractionated heparin containing components of varying degrees of activity, from highly active to relatively inactive, with cyanogen bromide to obtain an activated heparin intermediate;

(b) contacting the activated heparin intermediate from step (a) with antithrombin-III to obtain a mixture of a covalently bound complex of heparin and antithrombin-III (Hep—AT-III complex), free heparin and free antithrombin-III; and (c) processing the mixture of the covalently bound heparin—antithrombin-III complex, free heparin and free antithrombin-III from step (b) to separate free therefrom heparin to obtain a mixture of the covalent Hep—AT-III complex and free AT-III; and (d) processing the mixture from step (c) to separate therefrom free AT-III to obtain the covalently bound Hep—AT-III complex free of unbound, uncomplexed heparin and antithrombin.

It is also within the scope of this invention to perform the separations accomplished in steps (c) and (d) in a single step. For example this combination of steps (c) and (d) in a single step may be accomplished as described in Hoylaerts et al mentioned above.

Most preferably, the process for producing a covalently bound heparin—antithrombin-III complex useful for anticoagulant therapy according to the invention comprises the steps of:

(a) contacting unfractionated or fractionated heparin containing components of varying degrees of activity, from highly active to relatively inactive, with cyanogen bromide to obtain an activated heparin intermediate;

(b) contacting the activated heparin intermediate from step (a) with antithrombin-III to obtain a mixture of a covalently bound complex of heparin and antithrombin-III (Hep—AT-III complex), free heparin and free antithrombin-III;

(c) contacting the mixture of the covalently bound heparin—antithrombin-III complex, free heparin and free antithrombin-III from step (b) with a Concanavalin A (Con A)-Sepharose chromatographic column to obtain free heparin in the effluent and to retain the covalent Hep—AT-III complex and free AT-III bound on the Con A-Sepharose column;

(d) eluting the Con A-Sepharose column having the covalent Hep—AT-III complex and free AT-III retained thereon from step (c) with a carbohydrate solution having sufficient carbohydrate concentration to effect separation of the covalent Hep—AT-III complex and free AT-III from the column;

(e) contacting the covalent Hep—AT-III complex and free AT-III eluate from step (d) with a Heparin—Sepharose column to obtain in the eluate the free covalent Hep—AT-III complex and to retain the free AT-III bound on the Heparin—Sepharose column; and (f) recovering from the eluate of step (e) the covalently bound Hep—AT-III complex free of unbound, uncomplexed heparin and antithrombin.

It has been observed previously that antithrombin preferentially binds to high affinity heparin species, of high molecular weight or of low molecular weight, to form stable non-covalent complexes despite the presence of large excesses of inactive heparin species. By making use of this property of selectivity of antithrombin for highly active heparin species, it is an aspect of this invention to produce the covalent complex of antithrombin and "active" heparin species especially from pools of heparin which have not been pretreated by affinity fractionation or fragmentation techni-ques to isolate the active heparin species (i.e. "fractionated" heparin) or from fractionated It is advantageous, and accordingly preferred, to omit the step of isolating the "active" heparin species in the process according to the invention.

It is another aspect of this invention to employ a simple, straight forward activated form of heparin, which is "active" to undergo coupling with antithrombin, utilizing cyanogen bromide to effect the covalent linkage to antin. This activation and coupling is believed to involve the chemical. linkage having the nature described by Axen et al, *Eur. J. Biochem.*, 18, 351 (1971). Kohn et al, *Biochem. Biophys. Res. Commun.*, 107(3), 878 (1982) and *Enzyme Microbiol. Technology*, 4, 161, (1982), also describe the cyanogen bromide activation and coupling chemistry involving heparin and amino groups of proteins.

In the following description, emphasis is directed to the more preferred process of the invention. Following the methods described in Marshall et al, *J. Biol. Chem.*, 254 (4), 1081 (1976) and Tam et al, *Proc. Natl. Acad. Sci.*, 73 (b), 2128 (1976), to a stirred aqueous solution of heparin in water adjusted to pH of about 9.0 to 13.0, preferably 10.0 to 12.0, there is added cyanogen bromide to obtain an activated heparin intermediate. Usually, about 1 to 2 parts of heparin are used per 0.05 to 1 part of cyanogen bromide. Preferably, about 1 to 2 parts of heparin are used per 0.2 to 0.5 part of cyanogen bromide.

The activation step is carried out at a temperature of from about 2° to 35° C., preferably about 5° to 20° C., for a reaction period of about 5–60 minutes, preferably about 15–30 minutes.

The solution of the activated heparin intermediate, adjusted to a pH of about 8–10.5, preferably about 9.0–9.8, is then mixed with a solution containing about 1 to 2 parts of purified antithrombin-III (AT-III) per 10 to 30 parts of heparin in the activated heparin intermediate, the residual active groups being neutralized with glycine.

The temperature of this coupling reaction is about 2°–35° C., preferably about 5°–20° C., and the coupling reaction time is about 0.5–24 hours, preferably about 3–12 hours.

Next, the solution containing the covalently bound Hep—AT-III complex and, in addition, free heparin and free AT-III (including any non-covalent complex thereof which may be present), is applied to a lectin-containing, water-insoluble matrix prepared from a water-insoluble polymeric material and a lectin. As the water-insoluble polymeric material one may use any material to which the lectin can be bound; thus, one may use, by way of example and not limitation, certain cross-linked dextrans, crosslinked agarose, etc. For instance, one may employ Agarose or Sepharose 4B, or the like. The lectin is covalently bound to the matrix by means of cyanogen bromide or the like, using the method described by Cuatrecasas, *J. Biol. Chem.*, 1970, Vol. 245, pages 3059–3065. It should be noted that any method that covalently attaches a lectin to an insoluble matrix could be used to prepare the matrix of this invention. Lectins are carbohydrate-binding proteins of non-immune origin that agglutinate cells and/or precipitate complex carbohydrates and are isolated usually from seeds of plants. The preferred lectin for preparing the matrix for fractionating heparin is Concanavalin A. However, other D-mannose(D-glucose)-binding lectins may be used such as, for example, those described by Goldstein et al, in *Advances in Carbohydrate Chemistry and Biochemistry*, 1978, Vol. 35, pages 334–335. Most preferably, the solution containing the Hep—AT-III complex, free heparin and free AT-III is applied to a chromatographic Concanavalin A-Sepharose column (Con A-Sepharose) equilibrated with a buffer solution, for example, a buffer solution containing 0.25 M NaCl—0.05 M TRIS at pH 7.4. Buffers used for concanavalin-A Sepharose chromatography should also contain divalent cations which have been identified as necessary for maintaining lectin activity (e.g. 1 mM $CaCl_2$, 1 mM $MgCl_2$). Since AT-III, being a glycoprotein, binds to concanavalin-A through its glycosidic groups, both free AT-III and heparin-AT-III complexes are bound by the immobilized lectin. Free heparin is eluted off in a wash buffer containing a sufficiently high ionic strength to prevent any weak, non-specific interactions between non-antithrombin-bound heparin and the lectin itself (e.g. 0.25 M NaCl). High affinity heparin which is bound to antithrombin in a non-covalent fashion (i.e. by electrostatic interaction) is also removed at this step by washing the affinity matrix with a buffer containing a sufficiently high ionic strength (e.g. 1 M NaCl) to disrupt these heparin-antithrombin interactions.

Then, the covalently bound Hep—AT-III complex and the free AT-III are separated from the lectin-containing matrix, for example, from the Con A -Sepharose column, by contacting the lectin-containing matrix with a carbohydrate having sufficient molar strength to displace the complex and free AT-III. Generally, about 0.02–0.5 M aqueous solution of carbohydrate at a pH of about 6.0–8.5 is applied to effect the separation of the complex and AT-III from the lectin-containing matrix, for example, the Con A-Sepharose column. Suitable carbohydrates include glucopyranosides, manopyranosides and fructopyranosides. For example, 0.2 M mannoside may be used to conveniently effect this separation. As the carbohydrate, there may be used any one of the carbohydrates disclosed in Goldstein et al, in "Advances in Carbohydrate Chemistry and Biochemistry", 1978, Vol. 35, pages 334–335. Mono- and disaccharides also may be employed to separate the complex from the matrix and are preferred in this particular step. Thus, one may use, by way of example and not limitation, glucose, maltose, mannose, galactose, fructose, lactose, sucrose, and the like. It is within the compass of the invention to employ sugar alcohols such as mannitol, sorbitol, and the like to displace the Hep—AT-III complex and free AT-III from the lectin-containing matrix, for example, the Con A-Sepharose column.

Next, optionally after the carbohydrate solution of the covalently bound heparin—AT-III complex and free AT-III has been treated to reduce its carbohydrate concentration by conventional means such as dialysis, diafiltration and the like, the mixture of the complex and free AT-III in aqueous solution is applied to an affinity chromatography column having greater affinity for free AT-III than for the covalent Hep—AT-III complex, for example, a heparin-sepharose column. A gradient elution is carried out from 0.05 M TRIS-0.05 M NaCl, pH 7.4 to 0.05 M TRIS-1.5 M NaCl, pH 7.4. The covalently bound heparin—AT-III complex is thereby eluted from the column whereas the free AT-III is retained in a reversible complex on the heparin—Sepharose column.

The eluate containing the covalently bound heparin—antithrombin-III complex, Hep—AT-III, may then be processed to put it in condition for use. Generally, the eluate is concentrated to reduce its water content by conventional means. Also, if desired, carbohydrate remaining in solution in the eluate is then removed by conventional means, for example, dialysis, diafiltration, etc. The resulting concentrates containing the covalently bound Hep—AT-III complex can be formulated into pharmaceutical preparations for therapeutic use. The resulting covalently bound heparin—AT-III complex concentrate and pharmaceutical compositions containing the complex may be sterilized by conventional means, sterile-filtered, and treated to render them non-hepatitis infective.

Pharmaceutical preparations comprising the covalently bound, or covalently chemically coupled, Hep—AT-III complex may be sterilized to render the preparations non-hepatitis infective by conventional, known procedures, for example, heat treatment, chemical treatment, ultraviolet radiation treament and colloidal silica. For example, the preparations, in wet or dry state, may be heated at temperatures of about 60°–85° for a period of several minutes to several days. Optionally, the heat treatment procedure may be advantageously carried out in the presence of a heat stabilizing amount of at least one heat stabilizing agent. Suitable stabilizing agents include nonpolar anions with molecular weights greater than 80, sugars, reduced sugars, and amino acids. Examples of suitable nonpolar anions include salts of carboxylates, hydroxycarboxylates and amino acids such as sodium or potassium caprylate, caprate, oleate, laurate, valerate, acetylphenylalaninate, acetyleucinate, and acetyltryptophanate. Examples of suitable sugars include glucose, sucrose and maltose to name but a few, and examples of suitable reduced sugars include erythritol and mannitol. Examples of suitable amino acids include lysine, glysine, proline and glutamic acid to name but a few. By way of example without limitation, suitable conventional known sterilization processes include those disclosed in U.S. Pat. Nos. 3,041,242, 3,057,781, 3,227,626, 4,061,735, 4,137,307, 4,297,344, 2,705,230, 2,897,123, 3,284,301, 3,454,929, 4,379,085 and 4,370,264, and European Patent Publication No. 0058993, and in references disclosed in the patents.

The covalent Hep—AT-III complex product and concentrates thereof can be formulated into pharmaceutical preparations containing the complex and a pharmaceutically acceptable carrier. The term "pharmaceutical preparation" is intended in a broad sense herein to include preparations used for therapeutic purposes, for reagent purposes, for diagnostic purposes, for tissue culture purposes, and so forth. The pharmaceutical preparation intended for therapeutic use should contain a pharmaceutically acceptable and useful concentration of the complex to provide a therapeutically effective amount of the complex, i.e., that amount necessary for preventative or curative health measures. If the pharmaceutical preparation is to be employed as a reagent, then it should contain reagent amounts of complex. Similarly, when used in tissue culture or as a culture medium the pharmaceutical preparation should contain an amount of complex sufficient to obtain the desired growth.

It is a characteristic of compositions comprising the Hep—AT-III complex prepared in accordance with the present invention that they contain the complex in pharmaceutically useful amounts to provide therapeutically effective amounts.

To prepare them for intravenous administration the compositions are constituted usually in water containing physiologically compatible substances such as sodium chloride, glycine, sugar and the like in physiologically compatible concentrations and having a buffered pH compatible with physiological conditions. Generally, guidelines for intravenously administered compositions are established by governmental regulations.

Since many of the problems and limitations of current heparin therapy appear to result from inadequate levels of formed complexes with circulating antithrombin or too rapid clearance of infused heparin, the administration of the covalently bound Hep—AT-III complex solves this problem. It is to be understood that the covalently bound Hep—AT-III complex according to the invention contains as the heparin component highly active heparin species of high molecular weight and low molecular weight. It is also recognized in the art that although high molecular weight heparin is the more active, low molecular weight heparin is cleared less rapidly. As mentioned above, fractionated or unfractionated heparin, preferably the latter because of process step savings, may be used in the process of the invention. Further, it is within the scope of the invention to isolate that highly active low molecular weight heparin component to take full advantage of the low clearance rate. Thus, the levels of the Hep—AT-III complex obtained would not be subject to the conditions of the many equilibria which normally would prevent the full anticoagulant expression of heparin administered alone. Further, since no additional heparin would be given other than that bound to the antithrombin, it is to be expected that side effects resulting from the interaction of heparin with other serum components would be greatly diminished. Also, in addition to the increased potency and resulting lowered dosage of heparin required, the dose response characteristics of the Hep—AT-III complex administration are expected to be much more predictable than with current methods.

Several advantages apply. First, circulating antithrombin levels not be decreased as a result of this anticoagulant therapy using the Hep—AT-III complex since, presumably, the binding sites for antithrombin on the heparin in the complex are occupied and the complex would not readily dissociate to give free heparin. Second, administration of antithrombin covalently complexed with heparin should be beneficial to congenital antithrombin deficients for whom complete restoration to normal circulating levels may be economically difficult, and the administration of heparin alone is ineffective.

The following examples are illustrative of but a few embodiments of the invention and are not to be construed as limiting in scope. All parts and percentages are by weight and temperatures are in degrees Celcius unless otherwise indicated.

Assay Methods

Antithrombin III.

The Lowry protein assay was used using human serum albumin as the standard (Lowry et al, *J. Biol. Chem.*, 1951, Vol. 193, pages 265-275). Additionally, antithrombin concentrations were calculated from the absorbance at 280 nm using an extinction coefficient of 6.5.

Heparin. Two assays were employed (a) Carbazole Assay: A quantitative assay for heparin based on a standard curve of uronic acid. A uronic acid content of 30% was assumed for heparin (Hook et al, *FEBS Letters*, 1976, Vol. 66, pages 90-93). The assay was described by Bitter et al, in *Anal. Biochemistry*, 1962, Vol. 4, pages 330-334.

(b) Azure A Method: A qualitative assay based on the method of Jacques et al, *J. Physiol. (London)*, 1949, Vol. 109, pages 41-48, (see also Lam et al, *BBRC*, 1976, Vol. 69, pages 570-577).

Anticoagulant Activity of Heparin.

The activities of all heparin fractions were related to a given U.S.P. reference standard (Research lot 18,055-1). A standard curve was established with the above heparin, and all heparin fractions of unknown activity were determined by comparison to this curve by the following scheme:

(1) A 200 µl sample containing antithrombin (approximately 30 µg/ml) and 200 µl of a heparin-containing solution were combined and warmed to 37°.

(2) A 200 μl sample of a solution containing thrombin (Pentex® bovine thrombin, Miles Laboratories, Inc.) at a level in excess of the antithrombin was added to the mixture of (1) above and rapidly mixed.

(3) After exactly 30 seconds, 200 μl of a solution of 1 mM S-2238 (H-D-Phe-L-Pip-L-arg-p-nitroanilide, Kabi Diagnostica, Sweden) and 0.5 mg Polybrene® (Aldrich Chemical Co., Inc.) was added to the mixture which was again rapidly mixed.

(4) After exactly 60 seconds, 200 μl of 50% acetic acid was added to stop the esterolytic reaction.

(5) The U.V. absorbance of each sample was determined at 405 nanometers (nm).

EXAMPLE 1

Preparation of the Covalently Bound Hep—AT-III Complex

Heparin, 1 g (heparin sodium, Scientific Protein Labs., source porcine intestines, 167.7 USP units/mg) was chemically covalently coupled to 442 units (S-2238) of purified human antithrombin III prepared from Cohn Fraction IV-1("AT-III") (S-2238/$A_{280}$=8.7) by first dissolving the heparin in 100 ml of water at pH 10.7 and 20° C. and then adding to the solution 0.40 g of cyanogen bromide. The pH of the resulting solution of heparin and cyanogen bromide was adjusted to 10.7 and maintained at 20° C. for 40 minutes. This solution was dialyzed against pH 9.0 water (so adjusted with 1 M $Na_2CO_3$) for 3 hours at 20° C. Purified human antithrombin-III, 80 mg, was added to the solution. The pH of the resulting mixture was adjusted to and maintained at 9.4 and the temperature held a 5° C. for 18 hours to permit the coupling reaction to proceed. There was obtained 400 ml of solution containing the covalently bound Hep—AT-III complex, free heparin and free AT-III having an $A_{280}$=0.5. Forty five (45) ml of this solution was applied to a 30 ml Con A-Sepharose column (column size 2.5×6.5 cm) prepared by suspending Concanavalin A-Sepharose (Pharmacia Corp., Piscataway, NJ) in a buffer solution and equilibrated with the buffer solution containing 0.25 M NaCl and 0.1 M TRIS (tri-[hydroxymethyl]aminomethane), pH 7.4. The column was then washed with about 60 ml of aqueous 1 M NaCl solution to elute off free heparin. Analysis of the wash confirmed the presence only of free heparin.

Then, the Con A-Sepharose column was eluted with about 60 ml of aqueous 0.2 M mannoside solution to remove the Hep—AT-III complex and free AT-III from the column. Next, 32 ml of the mannoside eluate was applied to a 2.5×6.5 cm Heparin-Sepharose CL-4B column prepared by suspending 30 gm of Sepharose (Pharmacia Corp.) in a buffered aqueous solution of 0.05 M TRIS-0.05 M NaCl at pH 7.4.

A gradient elution was carried out from 0.05 M TRIS—0.05 M NaCl, pH 7.4 to 0.05 M TRIS—1.5 M NaCl, pH 7.4. From peak heights, it was estimated that 40% of the total starting protein was in the void volume, this fraction representing the protein (AT-III) that was covalently bound to heparin.

The presence of the two components, heparin and antithrombin-III, in the mannoside eluate was confirmed by immunoelectrophoresis and crossed immunoelectrophoresis evaluation.

EXAMPLE 2

Preparation of a Mixture of the Covalently Bound Hep—AT-III Complex and Free AT-III By following substantially the procedure described in Example 1, 4 g of heparin (heparin sodium) was covalently bound, or coupled, to 884 units of purified AT-III (S-2238/$A_{280}$=8.7) by first dissolving the heparin in 400 ml of water at pH 10.7-11.0 and 20° C. and then adding to the solution 1.60 g of cyanogen oromide. The pH of the resulting solution of heparin and cyanogen bromide was adjusted to 10.7 and maintained at 20° C. for 35 minutes. This solution was dialyzed against pH 9.0 water (pH adjusted with 1 M $Na_2CO_3$) for 3 hours at 20° C. 160 mg of purified human antithrombin-III was added to the solution. The pH of the resulting mixture was adjusted to and maintained at 9.4 and the temperature held at 5° C. for 18 hours to permit the coupling reaction to proceed. There was obtained 400 ml of solution containing the covalently bound Hep—AT-III complex, free heparin and free AT-III having an $A_{280}$=0.25. Forty five (45) ml of this solution was applied to a 30 ml Con A-Sepharose column (column size 2.5×6.5 cm) prepared by suspending Concanavalin A-Sepharose (Pharmacia Corp., Piscataway, N.J.) in a buffer solution and equilibrated with the buffer solution containing 0.25 M NaCl and 0.1 M TRIS (tri-[hydroxymethyl]aminomethane), pH 7.4. The column was then washed with about 60 ml of aqueous 1 M NaCl solution to elute off free heparin. Analysis of the wash confirmed the presence only of free heparin.

Then, the Con A-Sepharose column was eluted with about 65 ml of aqueous 0.2 M mannoside solution to remove the Hep—AT-III complex and free AT-III from the column. This absorption/elution scheme on the Con A-Sepharose column was repeated to obtain 130 ml of the mannoside eluate. This eluate, having $A_{280}$=0.37, was then dialyzed against 0.15 M NaCl and concentrated by ultrafiltration to an $A_{280}$ 2.10. The concentrated eluate was sterile filtered through a 0.2 μ membrane filter.

Characterization of Covalent Heparin-Antithrombin Complexes.

The inhibitory capacities of the prepared covalent complexes were examined with bovine thrombin and human Factor Xa. For this purpose, heparin-cofactor assays were run employing normal human plasma as a source of antithrombin and monitoring the extent of enzyme inactivation in the presence of 1 unit/ml heparin. Covalent heparin-antithrombin complexes were assayed against the standard curve without the addition of heparin. In each case, an inhibitory capacity was observed (expressed as plasma AT-III units per mg of antithrombin) which indicated both a high degree of inhibitor purity and inhibitory activity. The absence of added heparin in these determinations suggested that the covalently bound heparin was sufficient to promote essentially complete utilization of the inhibitor.

In the presence of heparin, the electrophoretic migration of antithrombin is significantly faster than in the absence of the mucopolysaccharide. Covalent antithrombin-heparin complexes were analyzed by cross immunoelectrophoresis without the addition of additional heparin to determine the relative proportions of slow and fast-moving antithrombin species. Nearly all of the antithrombin present in the covalent complex migrated as a fast-moving species, suggesting that the antithrombin was fully complexed with heparin. A similar result was obtained with single dimension immunoelectrophoresis.

Covalent complexes were also analyzed for the ability of heparin to induce an increase in ultraviolet fluorescence emission. A highly purified preparation of non-complexed inhibitor was also studied at an equivalent protein concentration in order to compare the magnitude of fluorescence enhancement caused by the addition of free heparin. Heparin induced the characteristic 30% increase in the fluorescence of free antithrombin but no fluorescence increase was observed when heparin was added to the covalent heparin-antithrombin complex. The relative fluorescence of the complex was, in fact, comparable to that obtained when heparin was added to the comparable level of free inhibitor. These results indicate that the covalent coupling of heparin to antithrombin in these complexes represents a productive binding interaction with the heparin-binding site of antithrombin fully saturated with mucopolysaccharide.

The rate at which the covalent heparin-antithrombin complexes inactivated human thrombin was compared to that of free antithrombin in the presence of high affinity heparin. Inhibitory rates were determined at equimolar concentrations of enzyme and inhibitor which were determined to be appropriate for the determination of the bimolecular rate constant using manual sampling methods. Protein concentrations of approximately $0.5-1 \times 10^{-8}$ M were employed. Inactivation curves encompassing residual thrombin levels of 30–100% were constructed at a series of different heparin concentrations. Residual thrombin levels were assayed with the chromogenic substrate S-2238 in the presence of polybrene for 8 minutes. For kinetic comparisons, a high affinity heparin species was employed which had been prepared from unfractionated commercial heparin. This heparin was assumed to be comparable to that present in the covalent heparin-antithrombin complex.

At a saturating concentration of free high affinity heparin and free antithrombin, a bimolecular rate constant of approximately $1.2 \times 10^9$ $M^{-1}$ min.$^{-1}$ was observed. Unexpectedly, when the covalent complex made in Example 1 (above) was tested at an equivalent antithrombin concentration but without any added heparin, a rate constant of approximately $4 \times 10^9$ $M^{-1}$ min.$^{-1}$ was obtained. The exact reason why the inhibitory rate constant of the covalent complex should be higher than that observed with the free components at saturating heparin levels is not clear. Possibly, however, the covalent nature of the complex circumvents certain equilibrium constraints which apply to the free component system and allow inactivation rates which are several times more rapid.

EXAMPLE 3

Preparation of the Covalent Bound Hep—AT-III Complex Using Low Molecular Weight Heparin Fraction There was prepared a covalently bound Hep—AT-III complex by following substantially the procedure described in Example 1 except for substituting for the unfractionated heparin a low molecular weight heparin fraction. This low molecular weight heparin fraction was obtained by chromatography of commercial porcine heparin on G-100. The fraction of heparin eluting at the position of 65–95% of the total eluted material was pooled and subjected to an additional gel chromatographic separation on Sephacryl S-300. Only the second half of the eluted material (50–100%) was pooled for use in coupling to antithrombin. The resulting reaction mixture containing free heparin, free antithrombin and the complex of antithrombin with low molecular weight heparin was fractionated on Con A-Sepharose and heparin-Sepharose as described above for the complexes formed with unfractionated heparin to obtain the covalently bound low molecular weight heparin—antithrombin-III complex.

Biological Data: Three rabbits were infused at the rate of 2 ml/kg body weight with covalently coupled Hep—AT-III complex from Example 2 above having heparin equivalency of 84 u/kg body weight together with a control rabbit which was infused at the rate of 2 ml/kg body weight with heparin (heparin sodium) having heparin equivalency of 200 u/kg body weight. Significant prolongation of aPTT (activated partial thromboplastin time, expression of anticoagulation effect) was noted for the experimental covalently coupled Hep—AT-III complex treated rabbits over the control rabbit for up to 3 hours following infusion.

What is claimed is:

1. A process for producing a covalently bound heparin—antithrombin-III complex useful for anticoagulant therapy which comprises the steps of:
    (a) contacting an aqueous solution, adjusted to a pH of about 9.0 to 13.0, containing about 1 to 2 parts of unfractionated or fractionated heparin containing components of varying degrees of activity, from highly active to relatively inactive, with 0.05 to 1 part of cyanogen bromide to obtain an activated heparin intermediate, wherein said solution is held at a temperature of from about 2° to 35° C. for a reaction period of about 5–60 minutes; and
    (b) contacting the aqueous solution, adjusted to a pH of about 8 to 10.5, containing the activated heparin intermediate from step (a) with about 1 to 2 parts of antithrombin-III per 10 to 30 parts of heparin in said intermediate at a temperature of about 2°–35° C. for a reaction period of about 0.5–24 hours to obtain a mixture of a covalently bound complex of heparin and antithrombin-III, free heparin and free antithrombin-III, wherein some of the free heparin and free antithrombin-III can associate together and be present in the form of a noncovalent, or ionic, association or complex.

2. A process according to claim 1 wherein the heparin used in step (a) is unfractionated heparin.

3. A covalently bound heparin—antithrombin-III complex produced by the process of claim 2.

4. A pharmaceutical composition for the treatment of thrombosis comprising an anti-thrombosis effective amount of the complex of claim 3 and a pharmaceutically acceptable carrier.

5. A process according to claim 1 including the additional step of:
    (c) processing the mixture of the covalently bound heparin—antithrombin-III complex, free heparin and free antithrombin-III from step (b) to separate therefrom free heparin to obtain a mixture of the covalent Hep—AT-III complex and free AT-III.

6. A process according to claim 5 wherein free heparin is separated from the mixture of the covalently bound heparin—antithrombin-III complex, free heparin and free antithrombin by means effective to separate free heparin from the said mixture selected from affinity chromatography, ion exchange chromatography, and electrophoresis techniques, and immobilized antibodies with affinity for antithrombin.

7. A process according the claim 6 wherein free heparin is separated from the said mixture of the covalently bound heparin—antithrombin-III complex, free heparin and free antithrombin by affinity chromatography techniques.

8. A process according to claim 7 wherein the affinity chromatography separation of free heparin from the mixture of the covalently bound heparin—antithrombin-III complex, free heparin and free antithrombin is carried out using a lectin-containing, water-insoluble matrix as the column adsorbent.

9. A process according to claim 8 wherein the lectin-containing, water-insoluble matrix is a Concanavalin A-Sepharose matrix.

10. A process according to claim 5 including the additional step of:
(d) processing the mixture from step (c) to separate therefrom free AT-III to obtain the covalently bound Hep—AT-III complex free of unbound, uncomplexed heparin and antithrombin.

11. A process according to claim 10 wherein free antithrombin-III is separated from the mixture of the covalently bound heparin—antithrombin-III complex and free antithrombin-III by means effective to separate free antithrombin-III therefrom selected from affinity chromatography, ion exchange chromatography, and electrophoresis techniques.

12. A process according to claim 11 wherein free antithrombin-III is separated from the mixture of the covalently bound heparin—antithrombin-III complex and free antithrombin-III by affinity chromatography techniques.

13. A process according to claim 12 wherein the affinity chromatography separation of free antithrombin-III from the mixture is carried out using a heparin-containing, water-insoluble matrix as the column adsorbent.

14. A process according to claim 13 wherein the heparin containing, water-insoluble matrix is a Heparin-Sepharose matrix.

15. A process according to claim 10 which further includes the step of sterilizing the covalently bound heparin—antithrombin-III complex to render the complex non-hepatitis infective.

16. A sterilized pharmaceutical composition for the treatment of thrombosis comprising an anti-thrombosis effective amount of the covalently bound heparin—antithrombin-III complex produced according to the process of claim 15 and a pharmaceutically acceptable carrier.

17. A covalently bound heparin—antithrombin-III complex produced by the process of claim 10.

18. A pharmaceutical composition for the treatment of thrombosis comprising an anti-thrombosis effective amount of the complex of claim 17 and a pharmaceutically acceptable carrier.

19. A covalently bound heparin—antithrombin-III complex produced by the process of claim 5.

20. A pharmaceutical composition for the treatment of thrombosis comprising an anti-thrombosis effective amount of the complex of claim 19 and a pharmaceutically acceptable carrier.

21. A covalently bound heparin—antithrombin-III complex produced by the process of claim 1.

22. A pharmaceutical composition for the treatment of thrombosis comprising an anti-thrombosis effective amount of the complex of claim 21 and a pharmaceutically acceptable carrier.

23. A process according to claim 1 which further includes the step of sterilizing the covalently bound heparin—antithrobmin-III complex to render the complex nonhepatitis infective.

24. A sterilized pharmaceutical composition for the treatment of thrombosis comprising an anti-thrombosis effective amount of the covalently bound heparin—antithrobin-III complex produced according to the process of claim 23 and a pharmaceutically acceptable carrier.

25. A process according to claim 5 which further includes the step of sterilizing the covalently bound heparin—antithrombin-III complex to render the complex non-hepatitis infective.

26. A sterilized pharmaceutical composition for the treatment of thrombosis comprising an anti-thrombosis effective amount of the covalently bound heparin—antithrombin-III complex produced according to the process of claim 25 and a pharmaceutically acceptable carrier.

27. A process for producing a covalently bound heparin—antithrombin-III complex useful for anticoagulant therapy which comprises the steps of;
(a) contacting an aqueous solution, adjusted to a pH of about 10.0 to 12.0, containing about 1 to 2 parts of unfractioned heparin containing components of varying degrees of activity, from highly active to relatively inactive, with 0.2 to 0.5 parts of cyanogen bromide to obtain an activated heparin intermediate, wherein said solution is held at a temperature of from about 5° to 20° C. for a reaction period of about 15–30 minutes;
(b) contacting the aqueous solution, adjusted to a pH of about 9.0 to 9.8, containing the activated heparin intermediate from step (a) with about 1 to 2 parts of antithrombin-III per 10 to 30 parts of heparin in said intermediate at a temperature of about 5°–20° C. for a reaction period of about 3–12 hours to obtain a mixture of a covalently bound complex of heparin and antithrombin-III, free heparin and free antithrombin-III;
(c) contacting the mixture of the covalently bound heparin—antithrombin-III complex, free heparin and free antithrombin-III from step (b) with a Concanavalin A Sepharose chromatographic column and eluting off free heparin in a wash buffer containing a sufficiently high ionic strength to prevent any weak, non-specific interactions between non-antithrombin-bound heparin and the lectin itself and containing divalent cations so as to obtain free heparin in the effluent and to retain the covalent Hep—AT-III complex and free AT-III bound on the Con A-Sepharose column;
(d) eluting the Con A-Sepharose column having the covalent Hep—AT-III complex and free AT-III retained thereon from step (c) with an aqueous carbohydrate solution having carbohydrate concentration in the range of about 0.02–0.5 M at a pH of about 6.0–8.5 sufficient to effect separation of the covalent Hep—AT-III complex and free AT-III from the column;
(e) contacting the covalent Hep—AT-III complex and free AT-III eluate from step (d) with a Heparin - Sepharose affinity chromatography column and carrying out a gradient elution from 0.05 M TRIS—0.05 M NaCl, pH 7.4 to 0.05 TRIS—1.5 M NaCl, pH 7.4 to obtain in the eluate the free covalent Hep—AT-III complex and to retain the free AT-III bound on the Heparin-Sepharose column; and (f) recovering from the eluate of step (e) the covalently bound Hep—AT-III complex free of unbound, uncomplexed heparin and antithrombin.

28. A covalently bound heparin—antithrombin-III complex produced by the process of claim 27.

29. A pharmaceutical composition for the treatment of thrombosis comprising an anti-thrombosis effective amount of the complex of claim 28 and a pharmaceutically acceptable carrier.

30. A process according to claim 27 wherein the carbohydrate is selected from glucopyranosides, manopyranosides, fructopyranosides, monosaccharides, disaccharides and sugar alcohols.

31. A process according to claim 27 which further includes the step of reducing the carbohydrate concentration of the covalently bound heparin—antithrombin-III complex recovered in step (f).

32. A process according to claim 27 which further includes the steps of reducing the carbohydrate concentration of, and concentrating, the covalently bound heparin—antithrombin-III complex recovered in step (f).

33. A process according to claim 32 which further includes the step of sterilizing the covalently bound heparin—antithrombin-III complex to render the complex non-hepatitis infective.

34. A sterilized pharmaceutical composition for the treatment of thrombosis comprising an anti-thrombosis effective amount of the covalently bound heparin—antithrombin-III complex produced according to the process of claim 33 and a pharmaceutically acceptable carrier.

35. A process according to claim 27 which further includes the step of sterilizing the covalently bound heparin—antithrombin-III complex to render the complex non-hepatitis infective.

36. A sterilized pharmaceutical composition for the treatment of thrombosis comprising an anti-thrombosis effective amount of the covalently bound heparin—antithrombin-III complex produced according to the process of claim 35 and a pharmaceutically acceptable carrier.

* * * * *